(12) United States Patent
Mohammadi

(10) Patent No.: US 10,806,420 B2
(45) Date of Patent: Oct. 20, 2020

(54) COMPUTER TOMOGRAPH

(71) Applicant: ESSPEN GmbH, Erlangen (DE)

(72) Inventor: Zahra Mohammadi, Erlangen (DE)

(73) Assignee: ESSPEN GmbH, Erlangen (DE)

( * ) Notice: Subject to any disclaimer, the term of this patent is extended or adjusted under 35 U.S.C. 154(b) by 0 days.

(21) Appl. No.: 16/482,702

(22) PCT Filed: Feb. 1, 2018

(86) PCT No.: PCT/EP2018/025024
§ 371 (c)(1),
(2) Date: Aug. 22, 2019

(87) PCT Pub. No.: WO2018/141485
PCT Pub. Date: Aug. 9, 2018

(65) Prior Publication Data
US 2020/0000423 A1 Jan. 2, 2020

(30) Foreign Application Priority Data
Feb. 1, 2017 (DE) .................. 10 2017 000 994

(51) Int. Cl.
*A61B 6/02* (2006.01)
*A61B 6/06* (2006.01)
(Continued)

(52) U.S. Cl.
CPC ............. *A61B 6/502* (2013.01); *A61B 6/025* (2013.01); *A61B 6/06* (2013.01); *A61B 6/4028* (2013.01);
(Continued)

(58) Field of Classification Search
CPC ......... A61B 6/025; A61B 6/032; A61B 6/035; A61B 6/06; A61B 6/4007; A61B 6/4021;
(Continued)

(56) References Cited

U.S. PATENT DOCUMENTS 6,647,092 B2 * 11/2003 Eberhard ................. G21K 1/04
378/150
7,177,391 B2 2/2007 Chapin et al.
(Continued)

FOREIGN PATENT DOCUMENTS

DE 102009017649 A1 10/2010
DE 102010011663 A1 9/2011
(Continued)

OTHER PUBLICATIONS

Greta R. Patzke et al.: "Oxidic Nanotubes and Nanorods—Anisotropic Modules for a Future Nanotechnology", Reviews, Angew. Chem. Int. Ed. 41: 5000-5015 (2002).
(Continued)

*Primary Examiner* — Thomas R Artman
(74) *Attorney, Agent, or Firm* — Merchat & Gould P.C.

(57) ABSTRACT

A computer tomograph (1) for mammographic x-ray imaging includes a MBFEX tube (20) and a flat-bed x-ray detector (30). Cathodes (40) are arranged in a fixed manner in rows in the MBFEX tube (20), the cathodes (40) being provided for the field emission of electrons. Geometry, radiation density and wavelength range of an x-ray beam (b) can be set. The MBFEX tube (20) is movable parallel (z) to the flat-bed x-ray detector (30). The flat bed x-ray detector (30) includes a moveable x-ray screen (31), the opening of which can be set. Using the x-ray screen (31), an imaging area (A) on the detector surface (D) of the flat-bed x-ray detector (30) can be selected and moved. Compared to conventional computer tomographs having rotating x-ray components, the computer tomograph (1) has a lighter and more compact design, with which a particularly small focal spot size is achieved.

15 Claims, 6 Drawing Sheets

(51) Int. Cl.
    *A61B 6/00*     (2006.01)
    *H01J 35/06*     (2006.01)
    *H01J 35/12*     (2006.01)
    *H01J 35/14*     (2006.01)

(52) U.S. Cl.
    CPC .......... *A61B 6/4078* (2013.01); *A61B 6/4085* (2013.01); *A61B 6/54* (2013.01); *H01J 35/064* (2019.05); *H01J 35/065* (2013.01); *H01J 35/066* (2019.05); *H01J 35/13* (2019.05); *H01J 35/14* (2013.01); *H01J 35/147* (2019.05); *H01J 2235/068* (2013.01); *H01J 2235/086* (2013.01); *H01J 2235/1204* (2013.01); *H01J 2235/1266* (2013.01); *H01J 2235/1275* (2013.01)

(58) Field of Classification Search
    CPC ... A61B 6/4028; A61B 6/4233; A61B 6/4283; A61B 6/502
    See application file for complete search history.

(56) References Cited

U.S. PATENT DOCUMENTS

| | | | |
|---|---|---|---|
| 7,233,644 B1 | 6/2007 | Bendahan et al. | |
| 7,539,284 B2* | 5/2009 | Besson | A61B 6/032 378/147 |
| 7,751,528 B2 | 7/2010 | Zhou et al. | |
| 8,031,834 B2* | 10/2011 | Ludwig | A61B 6/466 378/22 |
| 2003/0138078 A1* | 7/2003 | Eberhard | G21K 1/04 378/145 |
| 2004/0066904 A1* | 4/2004 | Eberhard | G21K 1/04 378/147 |
| 2008/0118023 A1* | 5/2008 | Besson | A61B 6/4028 378/8 |
| 2009/0022264 A1* | 1/2009 | Zhou | A61B 6/025 378/5 |
| 2010/0091940 A1* | 4/2010 | Ludwig | A61B 6/502 378/22 |
| 2012/0286692 A1 | 11/2012 | Beckmann et al. | |
| 2020/0000423 A1* | 1/2020 | Mohammadi | A61B 6/4007 |

FOREIGN PATENT DOCUMENTS

| | | |
|---|---|---|
| DE | 102010062541 A1 | 6/2012 |
| DE | 102011076912 B4 | 8/2015 |
| WO | 2007/038306 A2 | 4/2007 |
| WO | 2009/012453 A1 | 1/2009 |
| WO | 2014/076693 A1 | 5/2014 |

OTHER PUBLICATIONS

Xin Qian et al.: "Design and characterization of a spatially distributed multibeam field emission x-ray source for stationary digital breast tomosynthesis", Med. Phys., 36 (10): 4389-4399 (2009).
International Search Report for PCT/EP2018/025024, dated Jun. 15, 2018.
International Preliminary Report on Patentability for PCT/EP2018/025024, dated Aug. 6, 2019.

* cited by examiner

COMPUTER TOMOGRAPH

This application is a National Stage Application of PCT/EP2018/025024, filed Feb. 1, 2018, which claims the benefit of priority to German Patent Application No. 10 2017 000 994.5, filed Feb. 1, 2017, which applications are incorporated herein by reference. To the extent appropriate, a claim of priority is made to each of the above-disclosed applications.

BACKGROUND OF THE INVENTION

The invention relates to a computer tomograph for mammographic x-ray imaging, wherein a rotation of an x-ray tube for the x-ray imaging is not necessary and which comprises a multibeam field emission x-ray tube, wherein the multibeam field emission x-ray tube is referred to hereafter as MBFEX tube (MBFEX=Multibeam Field Emission X-Ray). Such a computer tomograph is known, for example, from U.S. Pat. No. 7,751,528 B2, which is provided in particular for taking x-rays of the female breast.

SUMMARY OF THE INVENTION

Breast cancer is the most commonly occurring cancer type in women. Approximately 10% of women suffer from breast cancer during the course of their life. Between 30% and 40% of these patients die from it, wherein mammography is an effective instrument for early detection of breast cancer. Early detection can significantly reduce breast cancer mortality. In the breast cancer diagnosis, for example, digital breast tomosynthesis (DBT), a 3D imaging method, is used. DBT performance is improved in comparison to full-field digital mammography (FFDM) currently considered to be the gold standard. The latest clinical studies have shown that DBT technology offers better detectability of densifications in the female breast. However, its sensitivity with regard to calcification, which is critical for cancer identification, is lower.

Moreover, past mammography methods have a high error rate, for example, a very high positive error rate (70~90%) and negative error rate (~30%). This characteristic of two-dimensional mammography makes it difficult to distinguish a cancer from breast tissue lying above it. The interpretation of the results can be variable depending on the radiologist, in particular in the case of a dense breast. A higher error rate of false positive and false negative test results occurs, because dense overlapping tissue has an interfering effect on the identification of tumor-associated anomalies. For young women with hereditary mutations who want to undergo preliminary examinations in their early years, these limitations associated with mammography are particularly problematic.

The detectability of microcalcifications using a DBT system can depend on many factors and can be influenced disadvantageously, for example, by detector type, reconstruction and shooting parameters. Motion blurring due to source/detector movement and the movement of the patient during the shooting is a dominating factor in the lack of spatial resolution of the DBT system, that is to say the detection of small microcalcifications. In addition, the female patient is exposed to a high radiation load.

The designs of all of the commercial DBT scanners are similar. A conventional x-ray tube mounted on a rotating arm moves in an arc above the compressed breast with an isocentric movement course in order to generate the sequence of projection images within a limited angular range. A mechanical construction, associated control software and precise angular measurement device are necessary in order to control the precise rotation of the x-ray tube. In this type of scanners, a complete tomosynthesis scan can take approximately 7 seconds to more than 1 minute. The time duration depends on the number of views recorded.

However, computer tomographs with x-ray tubes rotating synchronously with respect to one another exhibit considerable disadvantages. The mechanical instability caused by acceleration and deceleration of the source limits the speed at which the x-ray tube can be moved from one position to the next. The more rapid the scanning speed is, the greater the motion blurring. This effect is particularly serious in the case of a breast with a dense breast. For uniform and geometrically precise rotation, a complex mechanism with high space requirement is necessary. A mechanically occurring rotation moreover results in relatively slow rotation speeds and thus a longer shooting time. Such devices are very cost intensive both in terms of production and also in terms of maintenance due to the susceptibility to failure of the mechanism. The high energy consumption in particular should be emphasized.

One possibility for remedying the mentioned disadvantages, in particular for reducing the scanning time and also increasing the spatial resolution, consists in using a fixed row arrangement of x-ray emitters. In such a computer tomograph, the x-ray emitters are oriented toward the body to be examined and each is electrically controlled individually. The sequential actuation of the x-ray emitters thus replaces the rotation of an x-ray tube which was necessary in the past. Thereby, the projection views can be generated without mechanical movement. The motion blurring caused by the movement of the source can be eliminated completely. A row arrangement of individually actuatable x-ray emitters in general is described, for example, for a computer tomograph, in U.S. Pat. No. 7,233,644 B1 and in U.S. Pat. No. 7,177,391 B2 with multiple x-ray tubes, in DE 10 2011 076 912 B4 with a multibeam x-ray tube, and in DE 10 2009 017 649 A1 with a MBFEX tube.

For computer tomographs with a fixed arrangement of x-ray emitters, x-ray emitters designed as field emission x-ray tubes can be used. Such x-ray emitters have cathodes, for example, which contain carbon nanotubes, as also disclosed in U.S. Pat. No. 7,751,528 B2 and DE 10 2009 017 649 A1. The carbon nanotubes are used as cold cathodes for generating electrons which are then accelerated to generate x-ray sources on the anode. Such x-ray emitters can be designed to be particularly small and they can be arranged in a single vacuum tube; such a device represents a MBFEX tube wherein again a more compact design can be achieved.

In DE 10 2009 017 649 A1 and also in DE 10 2011 076 912 B4, a MBFEX tube is disclosed, wherein a plurality of cathodes are oriented toward a common anode.

In DE 10 2009 017 649 A1 and US 2012 0286692 A1, a closed-loop control of the cathodes of the MBFEX tube is proposed, in which an electric current between the cathodes and a grid is set with respect to a fixed voltage.

The aim of the invention is to provide a computer tomograph for mammographic x-ray imaging, which is further developed in comparison to the prior art, by means of which a small focal spot size and an improved examination possibility of a certain area of a cross section to be examined by x-ray (ROI=Region of Interest) can be implemented.

The aim is achieved according to the invention by a computer tomograph having the features of claim 1.

The proposed computer tomograph for mammographic x-ray imaging comprises an MBFEX tube and a flat-bed x-ray detector, wherein a plurality of cathodes in rows and at least one anode are arranged in a fixed manner in the MBFEX tube. The cathodes are provided for the field emission, directed onto the respective anode, of electrons extracted and accelerated in an electric field, and the respective anodes are provided for directed emission of x-rays as an x-ray beam. The number of cathodes corresponds to the number of x-ray sources, wherein at least one x-ray source can be generated on the respective anode. Here, the x-ray sources generated are also arranged in rows in the MBFX tube and oriented in their main x-ray emission direction onto the detector surface of the flat-bed x-ray detector. The flat-bed x-ray detector is provided for detection of x-rays as x-ray beams on the detector surface. On the MBFEX tube, for example, on an x-ray window, an adjustable collimator is arranged, by means of which the geometry of an x-ray beam can be set. Moreover, the MBFEX tube can be moved parallel to the flat-bed x-ray detector. The flat-bed x-ray detector itself comprises a moveable x-ray screen, the opening of which can also be set. Using the x-ray screen, an imaging area on the detector surface of the flat bed x-ray detector can be selected and moved.

The x-ray beams each have a direction with the maximum intensity of the emitted x-ray radiation which corresponds to the respective main x-ray emission direction. Such a main x-ray emission direction is provided in the case of all the x-ray sources that differ from a spherical radiation source.

In the proposed computer tomograph, an x-ray source can be implemented in terms of construction as a bounded surface, for example, as an ellipse or as a linear strip, on an anode; as desired, this can be achieved both by the nature of the respective cathode and also by adaptation of the electric field. By means of an appropriate focusing of the emitted electrons as electron beam, the form of the x-ray source can be selected, wherein the focusing corresponds to an adaptation of the electric field in a volume area between the respective cathode and the anode. By means of the proposed computer tomograph, the geometry and the radiation density of an x-ray beam can thus be set. The wavelength range of the emitted x-ray radiation and thus of the x-ray beam in addition can be set by focusing the electron beam and by the design of the cathodes.

In the proposed computer tomograph, for the x-ray image acquisition, in each case a cathode is electrically actuated sequentially by switching on and off, wherein, during the x-ray image acquisition, a common pulsed or temporally constant direct current voltage is applied to all the anodes. Due to the sequential actuation of the individual cathodes, in contrast to conventional computer tomographs according to the prior art, a mechanical rotation of x-ray sources is replaced. Here, the object to be examined is positioned between the MBFEX tube and the flat-bed x-ray detector. For example, a breast of a patient is positioned on a plate above the x-ray screen, wherein the plate is permeable to x-ray radiation.

In typical designs of the computer tomograph, the MBFEX tube is arranged above the detector. However, other arrangements of at least one x-ray tube and of at least one associated detector are also possible, for example, an arrangement of an x-ray tube under the associated detector, as is known in principle, for example, from DE 10 2010 011 663 A1.

By means of the x-ray screen, an imaging area on the detector surface can be set, for example, by moving and opening the x-ray screen under a breast resting on a plate. In an x-ray image acquisition, the object to be examined is stationary. The MBFEX tube can be moved parallel to the flat-bed x-ray detector. Thus, for each movement step of the MBFEX tube, in the selected imaging area, a cathode switching sequence of the cathodes and thus an x-ray image acquisition can be achieved, wherein, in each movement step, the MBFEX tube and the object to be examined carry out a relative movement with respect to one another.

For example, an x-ray image acquisition can occur in that cathodes which are successively adjacent to one another are electrically actuated sequentially. Likewise, the cathodes can also be operated in any other sequence, wherein the sequence can also be varied within the individual movement steps in the parallel direction.

The selection of a ROI can occur by adjusting the imaging area with the x-ray screen, by determining the movement steps in a subarea on the imaging area, and also by electrically actuating only the cathodes which are oriented onto the ROI. From the x-ray images thus obtained, which represent projection views, cross-sectional views and volume structures of the examined object can be generated by computer-assisted methods such as tomosynthesis or HEPC tomosynthesis (HEPC=High-Energy Phase Contrast) or filtered back-projection (FBP=Filtered Back-Projection).

In a projection, only the individual recording area containing the information, that is to say data, essential for the computer-assisted image generation is selected. Artifacts or poorly resolved areas are thus avoided. In particular, the time necessary for the computer-assisted image generation is considerably shortened, in that, on the detector surface of the flat-bed detector, the detection area and thus the imaging area are limited to the ROI by means of the x-ray screen.

Thus, with the proposed computer tomograph, and at the same time at minimal construction cost, high-resolution x-ray image acquisitions are possible in a shooting time which is shortened in comparison to the prior art. The higher the number of cathodes and thus x-ray sources arranged in a fixed manner in the MBFEX tube, the higher the image resolution which can be achieved in the entire ROI is. In general, the number of all of the cathodes in the proposed computer tomograph is at least equal to the number of projections for such a computer-assisted image generation.

In the case of a complete x-ray of an object under examination with the proposed computer tomograph, for example, the female breast, the MBFEX tube is preferably held stationary. In an examination of an ROI with the proposed computer tomograph, for example, inside a female breast, on the other hand, the MBFEX tube is preferably moved over the entire area of the ROI stepwise in the parallel direction, wherein, in each movement step, an x-ray image acquisition occurs.

Below, individual advantageous developments of the proposed computer tomograph are discussed with regard to the cathodes and the focusing of the electron beam in the MBFEX tube.

In a possible design of the proposed computer tomograph, the cathodes contain carbon nanotubes. Carbon nanotubes have a low field strength threshold value of less than 2 V $\mu^{-1}$ for the field emission of electrons. Due to the thus relatively low power consumption of the cathodes necessary for the field emission of electrons, the operation of such a computer tomograph is possible with a current supply which has only a relatively low capacity.

Alternatively or additionally to carbon nanotubes, the computer tomograph can comprise other nanorods which are designed for emitting electrons, for example. Examples here are hollow or solid nanorods which contain metal oxides, metal sulfides, nitrides, carbides and/or silicon. For the technical background, reference is made, for example, to the publication by Greta R. Patzke et al.: Oxidic Nanotubes and Nanorods—Anisotropic Modules for a Future Nanotechnology, Angew. Chem. Int. Ed. 2002, 41, 5000-5015.

To the extent that the electron emitter according to the invention contains a sulfide, the sulfide can be a metal sulfide, in particular molybdenum sulfide. As nitrides from which nanorods of the electron emitter can be entirely or partially constructed, mention is made in particular of boronitride, aluminum nitride, carbon nitride and gallium nitride. As carbide, silicon carbide is particularly suitable for producing nanorods, in particular nanotubes. Nanorods, in particular in the form of nanotubes, can also be produced out of silicon, optionally with doping elements. It is also possible to use nanorods containing cerium or lanthanum in the context of the production of the electron emitter of the computer tomograph. In this context, reference is made, for example, to the document WO 2014/076693 A1.

Cathodes functioning as electron emitter within the computer tomograph can also be designed as dispenser cathodes. Such cathodes are known, in principle, for example, from DE 10 2011 076 912 B4.

In another design of the proposed computer tomograph, the MBFEX tube has a grid device arranged in a fixed manner. In the grid device, an extraction grid electrode is common to all the electrodes, or in each case a separate extraction grid electrode is associated with each individual cathode. Here, each extraction grid electrode is arranged directly above the cathodes and provided for the field extraction of electrons from the cathodes. The extraction grid electrodes are preferably grounded when not in operation or they can preferably be switched galvanically with the cathodes. Moreover, the extraction grid electrodes are galvanically separated from all the other components of the MBFEX tube, whereby, particularly advantageously, arcing of the electrical field to these components is prevented, and the beam transport behavior of the electric voltage between the cathode and the extraction grid electrode is largely uncoupled. The extraction grid electrodes can be switched independently of the cathodes or optionally sequentially together with the cathodes. In an x-ray image acquisition, the extraction grid electrodes are switched as electrodes with a positive electric potential relative to the cathode; thereby, the field emission of electrons is substantially improved, and an electric arcing in the near vicinity of the cathodes is prevented. In case of high voltage conditioning, the MBFEX tube, the extraction grid electrodes are also switched as electrodes with a positive electric potential, wherein the cathodes are switched off. Thereby, the cathodes are protected from ion bombardment.

In a development of the last embodiment of the proposed computer tomograph, the grid device in each case has a separately associated focusing electrode directly above each extraction grid electrode for each individual cathode. The focusing electrodes are preferably grounded when not in operation. Moreover, the focusing electrodes are galvanically separated from all the other components of the MBFEX tube.

The focusing electrodes are provided for focusing the extracted electrons as electron beam. The focusing electrodes can be optionally electronically actuated sequentially together with the associated cathodes.

In an x-ray image acquisition, the focusing electrodes are in each case are switched as electrodes with a positive or negative electric potential, depending on whether a focusing or defocusing is to be achieved. A focusing of the electron beam can be set by the sign and the magnitude of the electrical potential as well as by the geometric form of the respective focusing electrode. In the case of a defined geometric form of the focusing electrodes, using the proposed computer tomographs, with each adjustment of an electric potential, respective x-ray image acquisitions can be achieved with different x-ray beams. Here, all the focusing electrodes have a respective identical electrical potential, so that, in an x-ray image acquisition, all the x-ray beams generated sequentially have the same geometry, radiation density and the same wavelength range. In particular, the focal spot size of the x-ray beam can thus be set with the focusing electrodes.

In the case of high-voltage conditioning of the MBFEX tube, the cathodes are switched off, and the extraction grid electrodes are exposed to a positive potential. As a result of this additional protective switching method, the cathodes can be shielded from ion bombardment even more advantageously.

In another embodiment, the proposed computer tomograph comprises more than one row arrangement of identical cathodes or of cathodes of different types. In this embodiment, one row arrangement includes no more than one type of cathode. In each case, cathodes of each type are oriented toward an anode. In an x-ray image acquisition, for example, only one type of cathode can be sequentially controlled in each case. In modified embodiments, cathodes of different types can be present within one and the same row of cathodes. In the simplest case, the term "type of cathode" can refer only to the area which a cathode takes up on a typically ceramic carrier. In such a case, all the cathodes of the different types can be switched in the same way. In other cases, the different cathodes differ, for example, with regard to their material or other features, while the externally visible contours of various types of cathodes in such cases can be uniform.

For example, the cathodes are of square, rectangular, round or ellipsoid design. To the extent that the cathodes differ in terms of their surface geometry from one another, differences with regard to the surface geometry and/or area size can exist. For example, if the cathodes are rectangular, then the cathodes can differ from one another by the rectangular area size. In the same way, different length/width ratios of different cathodes are possible.

Cathodes with different surface geometry or area size generate different electron beams. Thus, just by the selection of the cathodes, different x-ray sources and thus different x-ray beams of different geometries can be generated on the anode in question, for example, when the focusing electrodes are identical in terms of their construction form and arrangements above the cathodes and extraction grid electrodes and have the same electric potential. By means of the collimator, a refinement of the geometry of the respective selected x-ray beam can be achieved.

For example, in the case of otherwise identical extraction grid electrodes and focusing electrodes for computer-assisted x-ray imaging by HPEC tomosynthesis with the proposed computer tomograph, cathodes having a smaller area than for computer-assisted x-ray imaging by tomosynthesis are preferably selected. Thereby, in x-ray imaging by HPEC tomosynthesis, the focal spot size is particularly advantageously reduced and thereby a better image resolution of the ROI is achievable.

If, in this embodiment of the proposed computer tomograph, different cathodes are produced out of different materials, then they also differ with regard to the energy of the emitted electrons. This also applies when the cathodes, in terms of their construction and arrangement, are associated with identical extraction grid electrodes, and the same positive electric potential relative to the cathode is applied to all the extraction grid electrodes in an x-ray image acquisition. For example, cathodes of a first type have carbon nanotubes and cathodes of another type have tips made from tungsten or molybdenum.

Alternatively or additionally, by actuating the cathodes with different electrical voltages or different electrical currents, the energy of the emitted electrons and thus the energy of the emitted x-ray radiation can be set. For example, the forms of the cathodes differ in that they are provided each for a different actuation with regard to the electric current or the electric voltage. For example, the MBFEX tube of the proposed computer tomograph has two types of cathodes, wherein one type is provided for the operation with the stronger pulsed direct current, and the other type is provided for the operation with a weaker pulsed direct current. For example, the MBFEX tube of the proposed computer tomograph has two types of cathodes, wherein the two types are provided for operation with a pulsed square-wave direct current voltage, or with a pulsed square-wave direct current but with different switching frequency.

By means of a partial or comprehensive combination of different surface geometries, area sizes, different material constitution, and different current or voltage actuations, numerous different forms of cathodes can be implemented in the MBFX tube of the proposed computer tomograph. For example, one type of cathode is provided for the implementation of x-ray image acquisitions via tomosynthesis, and another type is provided for the implementation of x-ray image acquisitions via HEPC tomosynthesis.

In an additional preferred embodiment, the proposed computer tomograph is developed in that extraction grid electrodes and focusing electrodes of in each case one type are associated with each row arrangement of cathodes, wherein the row arrangements of cathodes differ by at least one type of extraction grid electrodes and/or at least one type of focusing grid electrodes.

Thus, even in the case of multiple arrangements consisting of cathodes of the same type, by selection of different types of extraction grid electrodes and/or different types of focusing grid electrodes, the geometry, the radiation density and also the wavelength range of an x-ray beam can be set, even if the types of the extraction grid electrodes and/or focusing electrodes differ only by an operation with a different electric voltage or a different electric current.

For example, different types of extraction grid electrodes are provided by different construction forms and/or by different arrangements above the cathodes. For example, different types of focusing electrodes can be implemented by different construction forms and/or by different arrangements above the cathodes and extraction grid electrodes.

In a preferred design of this development of the proposed computer tomograph, the MBFX tube comprises multiple arrangements consisting of cathodes of identical type with extraction grid electrodes of the same type, wherein the row arrangements of cathodes differ with regard to the types of focusing grid electrodes. In this embodiment of the proposed computer tomograph, the geometry, the radiation density and the wavelength range of an x-ray beam can be determined just by the selection and the operation of the focusing electrodes.

The multiple variation possibilities which relate in particular to the cathodes and their actuation enable the operation of the computer tomograph in a multi-dose mode. In such a mode, for example, at a certain time, a cathode is actuated in such a manner that it emits an electron current of 10 mA, wherein the anode voltage is set to 20 kV. These values remain constant, for example, over a pulse duration of 10 ms. The next pulse, which lasts 100 ms, can already be emitted with an electron current increased by a multiple, for example of 30 mA, wherein, for example, an anode voltage at the level of 100 kV is set. The resulting flexibility in the actuation of the computer tomograph enables an overall low-dose x-ray imaging which is correspondingly flexible and can be adapted to the individual case, with at the same time high imaging quality.

By means of the proposed computer tomograph, in the above presented developments, in an x-ray image acquisition, x-ray beams with identical focal spot size can thus be implemented in each case, wherein the respective focal spot size for each x-ray image acquisition can be set by prior adjustment of the focusing and selection of an arrangement of cathodes. The respective focal spot size is here also determined by the respective type of the cathodes, by the respective type of the grid extraction electrode and above all by the respective type of the focusing electrode.

For a computer-assisted x-ray imaging both by tomosynthesis and also by HPEC tomosynthesis, a temporally constant positive electric potential corresponding preferably to a first partial operation mode is applied to the anode in question, wherein the cathodes are preferably exposed to a uniform pulsed negative square-wave electric potential, and the extraction grid electrodes are preferably exposed to a uniform pulsed positive square-wave electric potential, with respect to the potential of the cathode. Thus, in these preferred operating modes, there is a uniform pulsed direct electric current.

For a computer-assisted x-ray imaging by tomosynthesis, one preferably selects a lower voltage between the anode in question and the cathodes but a stronger current than for a computer-assisted x-ray imaging by HPEC tomosynthesis. By means of these three preferred operating modes, both the anodes in question and also the cathodes are sufficiently protected from overheating.

For a computer-assisted x-ray imaging by tomosynthesis, electron beams and thus x-ray beams of lower energy than for a computer-assisted x-ray imaging by HPEC tomosynthesis are preferably selected, so that, for a tomosynthesis, the focusing electrodes preferably have a lower electric potential than for a computer-assisted x-ray imaging by HPEC tomosynthesis. Both in x-ray image acquisitions and also in the case of a conditioning of the MBFEX tubes, the focusing electrodes are preferably exposed to a temporally constant electric potential.

Below, individual advantageous developments of the proposed computer tomograph are explained with regard to the anode of the MBFEX tube.

In a preferred embodiment of the proposed computer tomograph, the cathodes in the MBFEX tube are oriented with regard to their main electron emission direction toward a common fixed anode. Preferably, the cathodes here are oriented toward the cathode in such a manner that the result is a row arrangement of x-ray sources on the anode; these x-ray sources correspond thus to x-ray emitters. Thus, in this design of the proposed computer tomograph, the cost of the switching technology is considerably reduced. Moreover, in this manner, a particularly compact and reduced-weight design of the MBFEX tube can be achieved.

In a design of the proposed computer tomograph, it is particularly advantageous if the common anode with which the cathodes are associated has an arc-shaped design and is oriented concavely toward the detector surface. Thus, with such an anode, the x-ray sources are also designed in the shape of an arc and oriented concavely toward the detector surface. With such an anode, dead angles around the parallel direction are avoidable. In an object to be examined, this enables a high resolution imaging of an ROI, even for areas which are covered partially by a partial layer which strongly absorbs x-ray radiation.

The anode, regardless of whether it overall has an elongate, straight, in particular cylindrical form or a curved form, is preferably designed as a fluid-cooled anode. Here, a coolant, in particular in the form of an electrically non-conductive oil, for example, a silicone oil, flows through a duct running in the longitudinal direction of the anode, wherein the back flow of the coolant from the anode occurs through an additional duct concentric to the first duct, so that a coolant connection for the inlet and outlet of the coolant is located just at one end of the anode. This design has the advantage that the mentioned connection for coolant can be connected by means of a single line arrangement to a high-voltage bushing of the x-ray tubes, whereby the number of high-voltage bushings is reduced.

Below, individual advantageous developments of the proposed computer tomograph are discussed with regard to the achievable adjustments of the MBFEX tubes, of the x-ray beam and of the imaging area.

In such a development of the proposed computer tomograph, an x-ray beam can be set, by means of a collimator, in the form of an x-ray cone beam having a circular or ellipsoid x-ray incidence area or in the form of an x-ray fan beam having a linear incidence area. The x-ray incidence area of the x-ray beam here relates to the detector surface on which the x-ray beam is incident. The x-ray incidence area of the x-ray beam covers the detector surface completely or at least partially. In an x-ray beam in the form of an x-ray cone beam, the main x-ray emission direction corresponds to the cone axis. In an x-ray beam in the form of an x-ray fan beam, the main x-ray emission direction runs through a fan plane which divides the x-ray incidence area lengthwise in half. For the x-ray image acquisition of the entire object to be examined, for example, a female breast, the x-ray beams are preferably set in the form of x-ray cone beams, wherein the MBFEX tube is held stationary.

Furthermore, the computer tomograph is designed so that the x-ray imaging area can be moved synchronously with the MBFEX tube in the parallel direction, and the x-ray beam can be set in the form of an x-ray fan beam. Here, the fan plane is perpendicular to the parallel direction. The incidence area completely covers the imaging area and is rectangular. The fan plane here is parallel to the long side of the x-ray imaging area and geometrically divides the x-ray imaging area in half. In this embodiment, the MBFEX tube of the proposed computer tomograph can be actuated synchronously with the x-ray screen. For the x-ray image acquisition of a ROI of an object to be examined, for example, a female breast, the x-ray beam is set preferably in the form of x-ray fan beams; here, for each movement step of the MBFEX tube and of the x-ray screen, in the x-ray imaging area selected for the ROI, a cathode switching sequence and thus an x-ray image acquisition can be achieved.

In another embodiment, the MBFEX tube can be set in terms of its spacing with respect to the detector surface in a vertical direction (typically referred to as y direction). Thus, for the purpose of adjustment, the incidence area of the x-ray beam can be set with regard to the imaging area before the performance of the computer-assisted x-ray image acquisition. In comparison to conventional solutions, it is thus possible to achieve, during the course of an HEPC tomosynthesis as well, x-ray image acquisitions with a higher anode voltage and at the same time a lower emission current by the adjustment of the MBFEX tube.

In contrast to known computer tomographs with a rotating x-ray tube, in x-ray images with the proposed computer tomograph, a focal spot size enlargement around the axial direction due to moving components is in principle ruled out.

The proposed computer tomograph, in particular in developments thereof, is characterized by a very compact and robust design. In comparison to the currently commercially available computer tomographs, the proposed computer tomograph, in particular with an MBFEX tube which comprises cold cathodes with carbon nanotubes, has the following advantages:

reduction of the radiation dose for the patients,
increase in the sensitivity and the specificity of imaging devices,
smaller weight and footprint,
improvement of the quality, and lowering of the costs (in particular the procurement and operating costs for such medical imaging systems) of health care providers.

The use of the proposed computer tomograph is in no way limited to medical diagnostics. The proposed computer tomograph is also suitable, for example, for x-ray imaging of inanimate objects, for example, for workpiece verification or product verification or for verifying the content of closed containers. The MBFEX tube of the proposed computer tomograph, in particular in the design in which a plurality of cathodes are associated with a common anode, can also be used for other computer tomographs.

BRIEF DESCRIPTION OF THE DRAWINGS

Below, the proposed computer tomograph is explained in greater detail in reference to a drawing in which three embodiment examples are summarized.

DETAILED DESCRIPTION OF THE PREFERRED EMBODIMENTS

Figure 1:
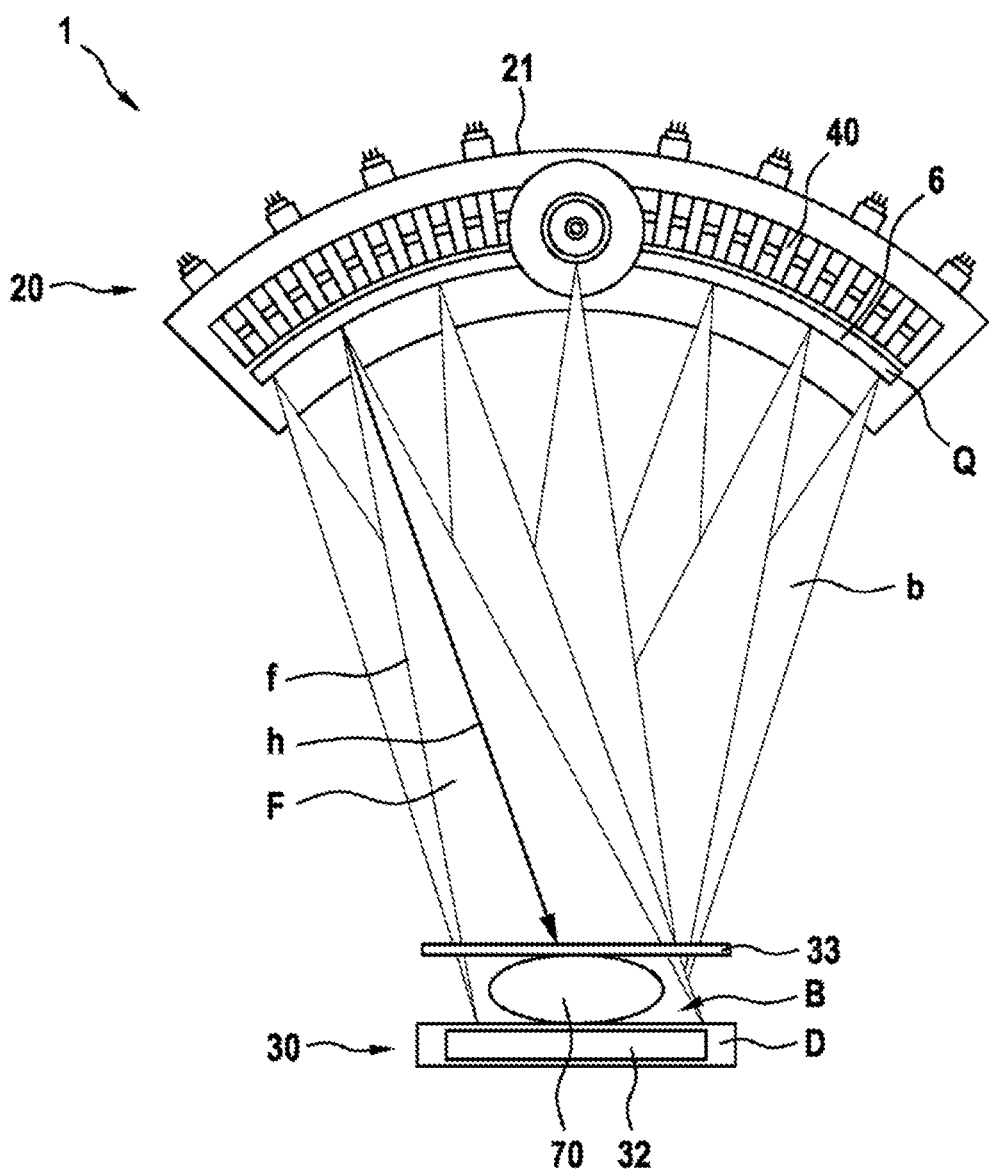
FIG. 1 shows a first embodiment example of a computer tomograph 1 in a diagrammatic view of the MBFEX tube 20 thereof.

All the embodiment examples of the proposed computer tomograph 1 explained below in reference to a drawing are provided for mammographic x-ray imaging. All the embodiment examples of the proposed computer tomograph 1 explained below comprise an MBFEX tube 20 and a flat-bed x-ray detector 30. A rectangular detector surface D of the flat-bed x-ray detector 30 is provided for the detection of x-rays.

In all the embodiment examples, the MBFEX tube 20 comprises a vacuum tube 21, an x-ray window 22, and a collimator 23, wherein the geometry of an x-ray beam b can be set with the collimator. The x-ray beams b have a direction with the maximum intensity of the x-ray radiation, which corresponds to a main x-ray emission direction h. In both embodiments of the proposed computer tomograph 1, by means of the collimator 23, the x-ray beam b can optionally be set as an x-ray cone beam c having a circular or ellipsoid x-ray incidence area B or as an x-ray fan beam f having a linear x-ray incidence area B, wherein the x-ray fan beam f has an x-ray fan plane F which divides the x-ray incidence area B in half lengthwise. The x-ray incidence area B covers the detector surface D partially or completely.

In all three embodiment examples of the proposed computer tomograph 1, the cathodes 40, 41, 42 are in each case arranged in row arrangements in a fixed manner in the form of an arc. In the first embodiment example, the MBFEX tube 20 comprises an arrangement of a plurality of identically shaped cathodes 40. In the second embodiment example, the MBFEX tube 20 comprises two arrangements each with a similar plurality of cathodes 41, 42 of two different types, wherein each of the two arrangements in each case comprises one type of cathode 41, 42, and the cathodes 41 of the first type are arranged in front of the cathodes 42 of the second type. The third embodiment example of the proposed computer tomograph 1 differs from the second one only in that the cathodes 41, 42, while being arranged in a row, are arranged alternatingly offset. In all three embodiment examples, the cathodes comprise multi-walled carbon nanotubes in a perpendicular preferential direction with respect to the respective cathode surface and have a design of rectangular form. The cathodes 41 of the first type and the cathodes 42 of the second type of the second and third embodiment examples differ by their area size.

In all the embodiment examples, the cathodes 40, 41, 42 are provided for the field emission of electrons, are oriented toward a common anode 6, and can optionally be exposed to a uniform pulsed negative potential up to 4 kV.

In all the embodiment examples, the anode 6 has a design in the form of an arc, it is oriented concavely toward the detector surface D and is arranged in the vacuum tube 21 in a fixed manner. In all the embodiment examples, the cathodes 40, 41, 42 are oriented toward the anode 6 in such a manner that, on the anode 6, a row arrangement of x-ray sources Q can be generated, wherein the x-ray sources Q also have a design in the form of an arc and are oriented concavely toward the detector surface D. In an x-ray image acquisition, in all three designs of the proposed computer tomograph 1, an x-ray image acquisition can be implemented by a sequential actuation of the cathodes 40, 41, 42.

In all three embodiment examples, the MBFEX tube 20 comprises a grid device 50, wherein the grid device 50 is oriented toward the cathode 6. The grid device 50 is arranged between the cathodes 40, 41, 42 and the anode 6 in the vacuum tube 21. The grid device 50 of all three embodiment examples comprises at least one extraction grid electrode 51, 53, 54 and at least one form of focusing electrodes 52, 55, 56.

The extraction grid electrodes 51, 53, 54 are arranged in a fixed manner directly above the cathodes 40, 41, 42 and are provided for the field extraction of electrons from the cathodes 40, 41, 42. The focusing electrodes 52, 55, 56 are also arranged in a fixed manner directly above the extraction grid electrode 51, 53, 54, they face the anode 6 and are provided for focusing the extracted electrons as an electron beam a onto the respective x-ray source Q to be generated.

Figure 4:
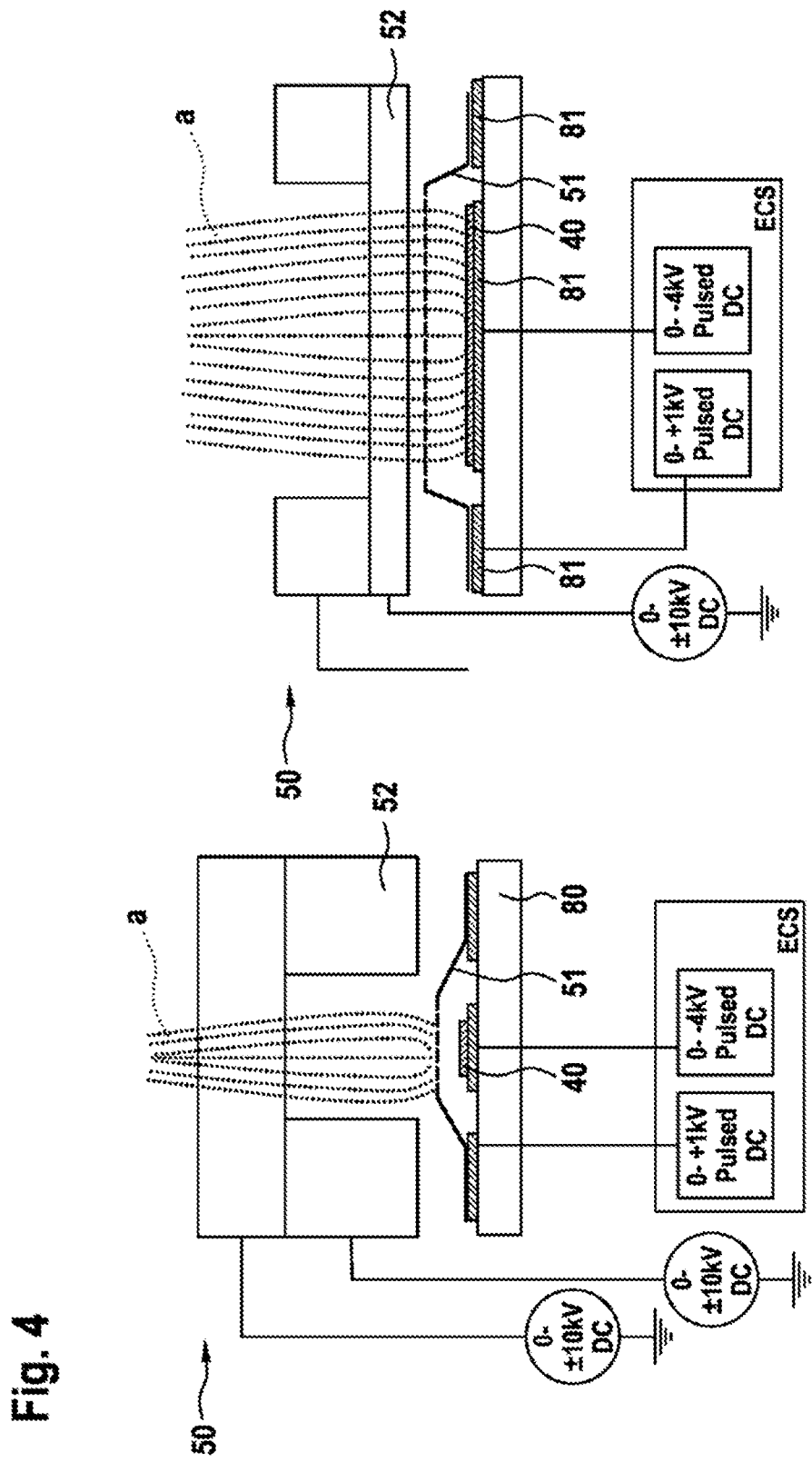
FIG. 4 shows a partial view of a grid device 50 of the MBFEX tube 20 of the first embodiment example of a computer tomograph 1.
Figure 5:
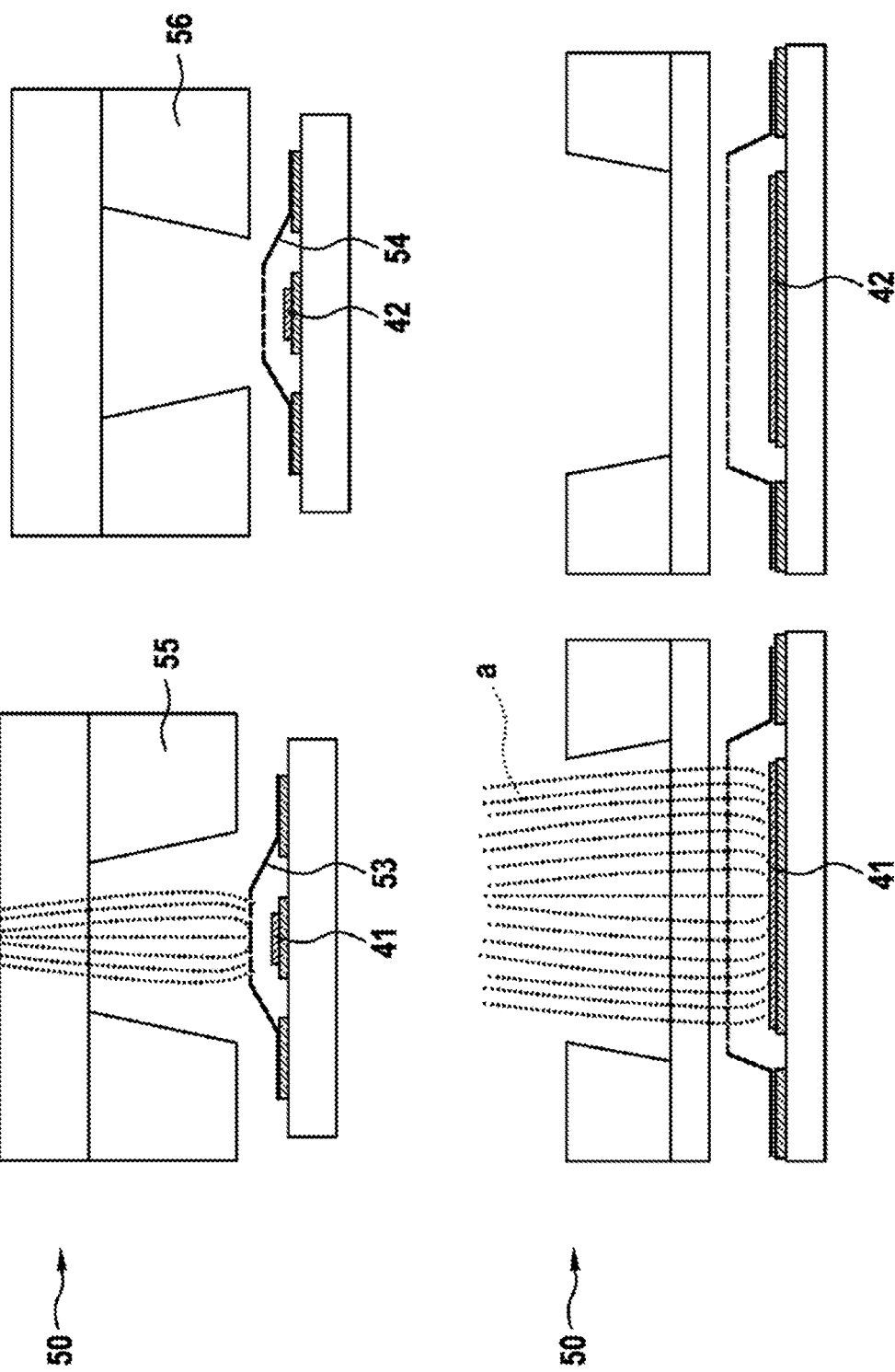
FIG. 5 shows a partial view of the grid device 50 of the MBFEX tube 20 of a second embodiment example of a computer tomograph 1.

In the first embodiment example, the grid device 50 comprises an extraction grid electrode 51 common to all the cathodes 40, wherein an individual focusing electrode 52 is separately associated with each individual cathode 40. In the second and third embodiment examples, the grid device 50 comprises an extraction grid electrode 53 of a first form, which is common to the cathodes 41 of the first type, and an extraction grid electrode 54 of a second form, which is common to the cathodes 42 of the second type, wherein in each case an individual focusing electrode 55 of a first form is separately associated with each individual cathode 41 of the first type, and in each case an individual focusing electrode 56 of a second form is separately associated with each individual cathode 42 of the second type. The extraction grid electrodes 51, 53, 54 and the focusing electrodes 52, 55, 56 are not drawn in FIG. 1, FIG. 2, FIG. 3 and in FIG. 6 and are explained in greater detail in reference to FIG. 4 for the first embodiment example and in reference to FIG. 5 for the second embodiment example. FIG. 4 and FIG. 5 are not true to scale. In FIG. 4, the grid voltage is indicated to be 0 to +1 kV, for example. Notwithstanding, during operation of the computer tomograph 1, a grid voltage in the range from zero to ±1 kV, for example, can be applied.

In all three embodiment examples of the proposed computer tomograph 1, the extraction grid electrodes 51, 53, 54 are grounded during when not in operation or, when in operation, they can be galvanically connected to the cathodes but are galvanically separated from all the other components of the MBFEX tube 20. The extraction grid electrodes 51, 53, 54 can optionally be exposed to a uniform pulsed positive potential of up to 1 kV.

In all three embodiment examples, the focusing electrodes 52, 55, 56 are also grounded when not in operation, but for operation they can be galvanically connected to the anode 6 but otherwise are galvanically separated from all the other components of the MBFEX tube 20, as shown representatively and schematically in FIG. 4. The focusing electrodes 52, 55, 56 can optionally be exposed to a temporally constant negative or positive potential of up to 10 kV.

For a computer-assisted x-ray imaging by tomosynthesis, a temporally constant potential of 40 kV is applied to anode 6, wherein between the anode 6 and the respectively switched cathode 40, 41, a uniform pulsed direct electric current of 30 mA flows. For a computer-assisted x-ray imaging by HPEC tomosynthesis, on the other hand, a temporally constant potential of 120 kV is applied to the anode in question, wherein between the anode 6 and the respective switched cathode 40, 42, a uniform pulsed direct electric current of 0.5 mA flows.

In all three embodiment examples of the proposed computer tomograph 1, in a computer-assisted x-ray imaging by tomosynthesis, a focal spot size having a diameter of 0.3 mm to 0.6 mm can be implemented, and, in a computer-assisted x-ray imaging by HPEC tomosynthesis, a focal spot size having a diameter of 0.1 mm can be implemented.

In all three embodiment examples, the proposed computer tomograph 1 comprises a current regulator, a device control, an electronic control system (ECS=Electronic Control System), a cathode high voltage source (CPS=Cathode Power Supply), an anode high voltage source (APS=Anode Power Supply), and a device control. The anode 6 is thus incorporated in a closed-loop current control, which includes a measurement of the current emitted by the cathodes 40, 42 for the purpose of the adjustment of the anode current to a certain value. The current regulator, the device control, the electronic control system, the cathode high voltage source, the anode high voltage source, and the device control are part of an electronic closed-loop control device. The current regulator, the device control, and the electronic control system represent an electronic control system.

The electronic closed-loop control device comprises a main electric circuit and a control loop, wherein the main circuit and the control loop are integrated in a direct current circuit. In the main circuit, the anode high voltage source is electrically connected to the anode 6 and to the current regulator, the current regulator is electrically connected to the device control, the device control is electrically connected to the electronic control system, the electronic control system is electrically connected to the cathode high voltage source, and the cathode high voltage source in parallel connection is electrically connected to the cathodes 40, 41, 42 and also to the respective grid device 50. In the control loop, the anode high voltage source is electrically linked by feedback to the control system. Here, the control system is provided at the same time for the sequential switching of the cathodes 40, 41, 42, for the closed-loop control of the extraction grid electrodes 51, 53, 54 and of the focusing electrodes 52, 55, 56 of the respective grid device 50 and also for the closed-loop control of the main circuit current, wherein, the electric voltage of the cathode high voltage source can be adapted to the main circuit current predetermined by the control system.

In all three embodiment examples, the MBFEX tube 20 can be moved in parallel direction z with respect to the flat-bed x-ray detector 30. In all the embodiment examples, the flat-bed x-ray detector 30 has a moveable x-ray screen 31, the opening of which can also be adjusted, wherein, using the x-ray screen 31, an imaging area A on the detector surface D of the flat-bed x-ray detector 30 can be selected and moved.

In all three embodiment examples of the proposed computer tomograph, the MBFEX tube 20 can be adjusted in terms of the spacing with respect to the detector surface D in a vertical direction y.

In an x-ray examination of a female human breast 70 as object to be examined, for example, the breast 70 is positioned between the MBFEX tube 20 and the flat-bed x-ray detector 30. In all the embodiment examples of the proposed computer tomograph 1, the breast 70 of a female patient is placed on a plate 32 above the x-ray screen 31, wherein the plate 32 is permeable to x-ray radiation. By means of a compression plate 33, the breast 70 is temporarily secured on the plate 32 for the x-ray examination.

The first embodiment example of the proposed computer tomograph 1 is explained in further detail below in reference to FIG. 1, FIG. 2, FIG. 3 and FIG. 4.

FIG. 1 shows a diagrammatic view of the MBFEX tube 20 of the first embodiment example of a computer tomograph 1. FIG. 1 is not true to scale. The vacuum tube 21, the x-ray window 22 and the collimator 23 of the MBFEX tube 20, the grid device 50 and also the x-ray screen 31 cannot be seen in FIG. 1. In FIG. 1, the x-ray beam b is drawn in the form of fan beams f which can be generated sequentially. The x-ray beams b are oriented in their main x-ray emission direction h toward the enclosed breast 70.

Figure 2:
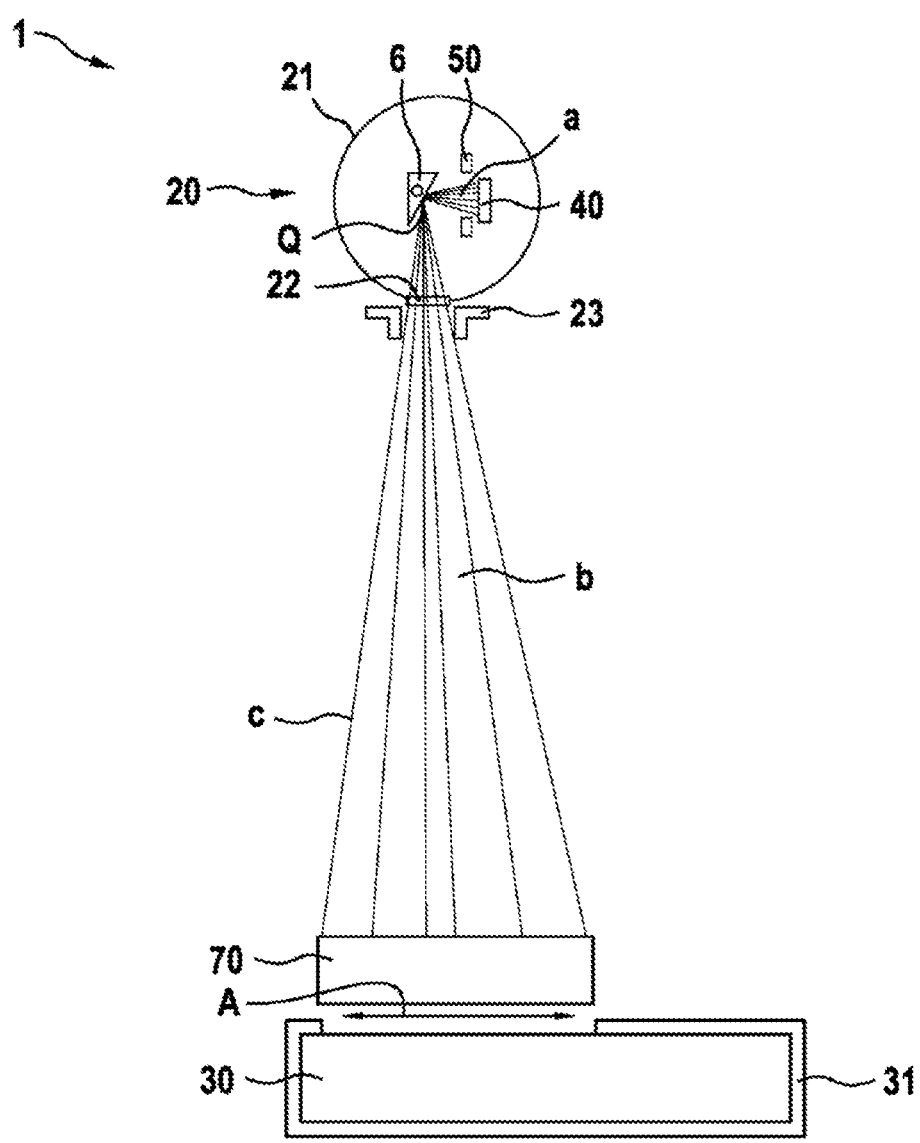
FIG. 2 shows the first embodiment example of a computer tomograph 1 with representation of an x-ray beam b in the form of a cone beam c.

FIG. 2 shows the proposed computer tomograph 1 in its first embodiment example in a side view. In FIG. 2, the computer tomograph 1 is shown diagrammatically during computer-assisted x-ray imaging of the entire breast 70 by tomosynthesis, wherein, by means of the collimator 23, all the x-ray beams b are set in the form of cone beams c, and the MBFEX tube 20 is held stationary. The imaging area A is set by means of the x-ray screen 31 in such a manner that it completely encloses the breast 70.

Figure 3:
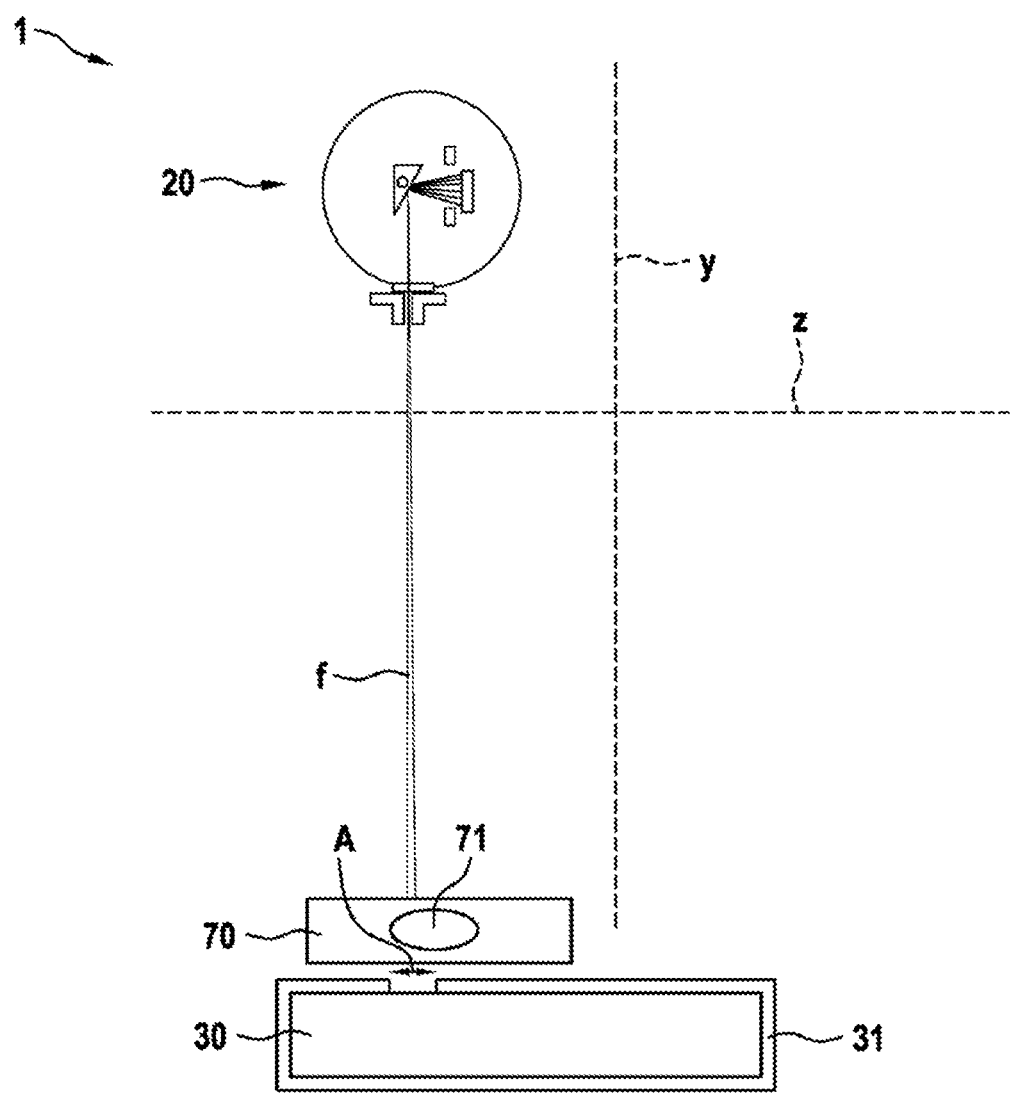
FIG. 3 shows the first embodiment example of a computer tomograph 1 with representation of an x-ray beam b in the form of a fan beam f.

FIG. 3 shows the proposed computer tomograph 1 in its first embodiment example also in a side view. In FIG. 3, the computer tomograph 1 is shown diagrammatically during computer-assisted x-ray imaging of a ROI 71 of the breast 70 by HPEC tomosynthesis, wherein, by means of the collimator 23, all the x-ray beams b are set in the form of fan beams f, wherein the respective x-ray fan planes F are perpendicular to the parallel direction z. In the x-ray image acquisition of the ROI 71, the imaging area A can be moved synchronously with the MBFEX tube 20 in the parallel direction z. The x-ray incidence area B covers the imaging area A completely and is rectangular. The x-ray fan plane F is here parallel to the long side of the imaging area A and divides the imaging area A geometrically in half. The MBFEX tube 20 is actuated during the x-ray image acquisition of the ROI 71 synchronously with the x-ray screen 31. For each movement step of the MBFEX tube 20 and the of the x-ray screen 31, in the imaging area A selected for the ROI 71, a switching sequence of the cathodes 40 and thus an x-ray image acquisition is achieved.

With the proposed computer tomograph 1 in its first embodiment, using only one arrangement of cathodes 40 of one type, in each case x-ray image acquisitions for two different computer-assisted methods for generating cross-sectional views and volume structures of the object to be examined can be achieved. For this purpose, for computer-assisted x-ray imaging by HPEC tomosynthesis, a higher negative electric potential than for computer-assisted x-ray imaging by tomosynthesis is applied to the focusing electrodes 52.

FIG. 4 shows a partial view of the grid device 50 of the first embodiment example of the proposed computer tomograph 1, which is limited to the exemplary representation of a cathode 40 with the focusing electrode 52 associated therewith. In FIG. 4, on the left, a partial view of the grid device 50 with respect to the longitudinal direction of the cathodes 40 and, on the right, a partial view of the grid device 50 with respect to the transverse direction of the cathodes 40 are represented; in the two partial views, the extraction grid electrode 51 is represented in a respective cross-sectional view. The grid device 50 and the cathodes 40 are arranged on a common ceramic carrier 80. The extraction grid electrode 51 and the cathodes 40 are each connected to the ceramic carrier 80 via a metal layer 81. The extraction grid electrode 51 is produced from tungsten. The metal layer 81 is provided for the electric contacting of the cathodes 40 and of the extraction grid electrode 51, via which the cathodes 40 and the extraction grid electrode 51 are electrically connected to the electronic control system. The electronic control system is diagrammatically drawn in FIG. 4. In FIG. 4, a cathode 40 during its electronic actuation together with the associated focusing electrode 52 is represented in the switched-on state, wherein the extraction grid electrode 51 is also switched-on, and the field line pattern of the electron beam a generated is drawn diagrammatically.

The second embodiment example of the proposed computer tomograph 1 is explained below in reference to FIG. 5. FIG. 5 also shows a partial view of the grid device 50, which is limited to the exemplary representation of two cathodes 41, 42 with the respective focusing electrodes 55, 56 associated therewith. In FIG. 5, at the top, a partial view of the grid device 50 with respect to the longitudinal direction of the cathodes 41, 42, and a partial view of the grid device 50 with respect to the transverse direction of the cathodes 41, 42 are represented; in the two partial views, the extraction grid electrodes 53, 54 are also represented in a respective cross-sectional view. The cathodes 41 of the first type have a smaller area than the cathodes 42 of the second type. In an x-ray image acquisition, either the cathodes 41 of the first type or the cathodes 42 of the second type are actuated sequentially, wherein the cathodes 41 of the first form are provided for a computer-assisted x-ray imaging by HPEC tomosynthesis, and the cathodes 42 of the second form are provided for a computer-assisted x-ray imaging by tomosynthesis. In FIG. 5, a cathode 41 during its electronic actuation together with the associated extraction grid electrode 53 and the associated focusing electrode 55 is represented in the switched-on state during computer-assisted x-ray imaging by HPEC tomosynthesis.

Figure 6:
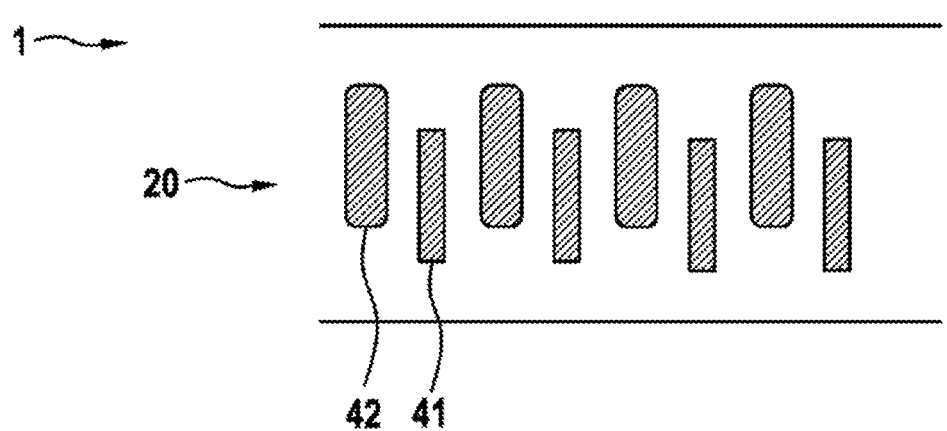
FIG. 6 shows a third embodiment example of a computer tomograph 1 with cathodes 41, 42 of two different types arranged in a row, alternatingly offset.

The third embodiment example of the proposed computer tomograph 1 is explained below in reference to FIG. 6. FIG. 6 is limited to the exemplary representation of a total of eight cathodes 41, 42 of the MBFEX tube 20. The grid device 50 cannot be seen in FIG. 6.

In all three embodiment examples of the proposed computer tomograph 1, dead angles around the parallel direction z can be avoided by means of the arc-shaped anode 6. Thus, in all the embodiment examples, each ROI 71 can be imaged around the parallel direction z completely, uniformly and with high resolution with at the same time a relatively low x-ray exposure of the object to be examined, as illustrated graphically in the drawn x-ray beam b as an example in FIG. 1, FIG. 2 and FIG. 3. The proposed computer tomograph 1, in all three embodiment examples, in particular the MBFEX tube 20, is characterized by a particularly compact design.

LIST OF REFERENCE NUMERALS

1 Computer tomograph
20 MBFEX tube
21 Vacuum tube
22 X-ray window
23 Collimator
30 Flat-bed x-ray detector
31 X-ray screen
32 Plate
33 Compression plate
40 Cathode
41 Cathode of a first type
42 Cathode of a second type
50 Grid device
51 Extraction grid electrode
52 Focusing electrode
53 Extraction grid electrode of a first form
54 Extraction grid electrode of a second form
55 Focusing electrode of a first form
56 Focusing electrode of a second form
6 Anode
70 Breast
71 ROI
80 Ceramic carrier
81 Metal layer
D Detector surface
b X-ray beam
h Main x-ray emission direction
c X-ray cone beam
f X-ray fan beam
B X-ray incidence area
F X-ray fan plane
Q X-ray source
a Electron beams
z Parallel direction
A Imaging area
y Vertical direction

The invention claimed is:

1. A computer tomograph for mammographic x-ray imaging, comprising: a MBFEX tube and a flat-bed x-ray detector, wherein a plurality of cathodes is arranged in a fixed manner in rows in the MBFEX tube, the cathodes being provided for field emission of electrons, and geometry, radiation density and wavelength range of an x-ray beam (b) are set, the MBFEX tube are movable parallel to the flat-bed x-ray detector, the flat bed x-ray detector comprising a moveable x-ray screen, the opening of the moveable x-ray screen is set, and, using the x-ray screen, an imaging area on a detector surface of the flat-bed x-ray detector is selectable and moveable.

2. The computer tomograph according to claim 1, wherein the cathodes contain carbon nanotubes.

3. The computer tomograph according to claim 1, wherein the cathodes contain nanorods for emitting electrons, which contain a substance selected from a group of substances consisting of metal oxides, metal sulfides, nitrides, carbides and silicon.

4. The computer tomograph according to claim 1, wherein the MBFEX tube has a grid device arranged in a fixed manner, wherein, in the grid device, an extraction grid electrode is common to all the cathodes or a separate extraction grid electrode is associated with each individual cathode, and each extraction grid electrode is arranged directly above the cathodes and is provided for field extraction of electrons.

5. The computer tomograph according to claim 4, wherein the grid device has a separately associated focusing electrode directly above each extraction grid electrode for each individual cathode, wherein each focusing electrode is provided for focusing extracted electrons as electron beam.

6. The computer tomograph according to claim 4, wherein extraction grid electrodes and focusing electrodes of one type are associated with each row arrangement of cathodes, wherein the row arrangements of cathodes differ from one another by at least one type of extraction grid electrodes and/or at least one type of focusing grid electrodes.

7. The computer tomograph according to claim 1, wherein the MBFX tube comprises a plurality of row arrangements of identical cathodes or of cathodes of different types, wherein each row arrangement comprises not more than one type of cathodes.

8. The computer tomograph according to claim 7, wherein the cathodes of different types differ from one another at least with regard to surface area that the cathodes occupy on a common carrier.

9. The computer tomograph according to claim 1, wherein multiple cathodes are oriented toward a common fixed anode (6).

10. The computer tomograph according to claim 9, wherein the anode is in a shape of an arc and directed concavely toward the detector surface.

11. The computer tomograph according to claim 9, wherein the anode is a fluid-cooled anode.

12. The computer tomograph according to claim 9, wherein the anode is part of a closed-loop control circuit for current-based current control, which includes a measurement of electron current emitted by the cathodes.

13. The computer tomograph according to claim 1, wherein, using a collimator, the x-ray beam is set as desired as an x-ray cone beam with a circular or ellipsoid x-ray incidence area or as an x-ray fan beam with a linear x-ray incidence area, wherein the x-ray fan beam comprises an x-ray fan plane which divides the x-ray incidence area lengthwise in half.

14. The computer tomograph according to claim 13, wherein the imaging area is moveable synchronously with the MBFEX tube in parallel direction, and the x-ray beam is set as an x-ray fan beam, wherein the x-ray fan plane is perpendicular to the parallel direction, the x-ray incidence area completely covers the imaging area, the imaging area is rectangular, the x-ray fan plane is parallel to a long side of the imaging area, the x-ray fan plane divides the imaging area geometrically in half, and the MBFEX tube is actuated synchronously with the x-ray screen.

15. The computer tomograph according to claim 1, wherein spacing of the MBFEX tube is set with respect to the detector surface in a vertical direction.

\* \* \* \* \*